United States Patent [19]
Heins et al.

[11] Patent Number: 6,027,723
[45] Date of Patent: Feb. 22, 2000

[54] *RHODOCOCCUS GLOBERULUS* STRAIN FOR CONTROLLING CORN ROOTWORM

[75] Inventors: Sherry Darlene Heins; Denise Carol Manker, both of Davis; Desmond Rito Jiménez, Woodland; Pamela Gail Marrone, Davis, all of Calif.

[73] Assignee: AgraQuest, Inc., Davis, Calif.

[21] Appl. No.: 08/915,343

[22] Filed: Aug. 22, 1997

[51] Int. Cl.[7] ..................................................... C12N 1/20
[52] U.S. Cl. ........................................ 424/93.4; 435/252.1
[58] Field of Search ......................... 435/252.1; 424/93.4

[56] References Cited

U.S. PATENT DOCUMENTS

| | | |
|---|---|---|
| 4,999,192 | 3/1991 | Payne et al. . |
| 5,187,091 | 2/1993 | Donovan et al. . |
| 5,208,017 | 5/1993 | Bradfisch et al. . |
| 5,208,159 | 5/1993 | Toda ..................................... 435/252.1 |

FOREIGN PATENT DOCUMENTS

WO 96/10083  4/1996  WIPO .

OTHER PUBLICATIONS

Johnson et al. (1993) "Insecticidal Activity of EG4961, a Novel Strain of *Bacillus thuringiensis* Toxic to Larvae and Adults of Southern Corn Rootworm (Coleoptera: Chrysomelidae) and Colorado Potato Beetle (Coleoptera: Chrysomelidae)," *J. Ecomonic Entomology* 86:330–333.

Estruch et al. (1997) "Transgenic Plants: An Emerging Approach to Pest Control," *Nature Biotechnology* 15:137–141.

Burgjeron and Biache (1966) "Alimentation au Laboratoire de *Perillus bioculatus* Fabr. Avec des Larves de Leptinotarsa Decemlineat a Say Intoxiquées par la Toxine Thermostable de *Bacillus thuringiensis* Berliner," *Entomophaga* II:279–284. An English summary is printed on p. 283.

Argauer et al. (199) "Evidence for a Novel Insecticidally Active Exotoxin Produced by the HD 116 Strain of Bacillus," *J. Entomol. Sci.* 26:205–213.

Lüthy (1980) "Insecticidal Toxins of *Bacillus thuringiensis*," *FEMS Mirobiol. Lett.* 8:1–7.

Forsberg et al. (1976) "*Bacillus thuringiensis*: Its effects in Environmental Quality," *National Research Council of Canada, NRC Associate Committee on Scientific Criteria for Environmental Quality, NRC 15385*, 16 pages total.

Stonard et al. (1994) "Microbial Secondary Metabolites as a Source of Agrochemicals," *ACS Symposium Series*, Natural and Engineers Pest Management Agents 551:25–35.

Miller (1982) "Single Derivatization Method for Routine Analysis of Bacterial Whole Cell Wall Fatty Acid Methyl esters, Including Hydroxy Acids," *J. Clin Micriobiol.* 16:584–586.

Bochner (1989) "Sleuthing Out Bacterial Identities," *Nature* 339:157–158.

Yu et al. (1997) "The *Bacillus thuringiensis* Vegetative Insecticidal Protein Vip3 Lyses Midgut Epithelium Cells of Susceptible Insects," *Appl. Environ. Microbiol.*, 63:532–536.

Marrone et al. (1985) "Improvements in Laboratory Rearing of the Southern Corn Rootworm, *Diabrotica undecimpuncta howardi* Barber (Coleoptera: Chrysomelidae), on an Artificial Diet and Corn," *J. Econ Entomol.* 78:290–293.

Goodfellow et al., The Biology of the Actinomycetes, 1984, Academic Press, pp. 91–94.

*Primary Examiner*—Irene Marx
*Attorney, Agent, or Firm*—Antoinette F. Konski; Baker & McKenzie

[57] ABSTRACT

A novel pesticidal metabolite-producing *Rhodococcus globerulus* strain is provided. In addition, a supernatant of the novel strains with pesticidal activity is provided. A solvent-extractable metabolite produced by the novel strain of *Rhodococcus globerulus* with pesticidal activity against corn rootworms is provided. Also included are methods for protecting or treating plants from corn rootworm infestations comprising the step of applying to the plant an effective amount of the novel *Rhodococcus globerulus* strain, the metabolite produced by the novel strain or a combination thereof, optionally, further comprising applying another pesticidal metabolite-producing bacterial strain and/or a chemical pesticide.

10 Claims, 4 Drawing Sheets

| | FIG. 1A |
|---|---|
| | FIG. 1B |
| | FIG. 1C |

ID: 2905    AGRAQUEST-719    (48HR)    Date of run: 03-OCT-96 14:35:44
Bottle:19    SAMPLE    [AEROBE]

| RT | Area | Ar/Ht | Respon | ECL | Name | % | Comment 1 | Comment 2 |
|---|---|---|---|---|---|---|---|---|
| 1.449 | 3516953400 | 0.024 | ..... | 7.025 | SOLVENT PEAK ......... | ..... | < min rt | |
| 2.053 | 480 | 0.021 | ..... | 8.310 | | | < min rt | |
| 6.457 | 10290 | 0.034 | 0.997 | 13.999 | 14:0 ............. | 4.49 | ECL deviates -0.001 | Reference 0.001 |
| 7.743 | 462 | 0.034 | 0.964 | 14.901 | 15:1 w5c........ | 0.19 | ECL deviates -0.003 | |
| 7.885 | 5844 | 0.036 | 0.961 | 15.001 | 15:0 ............ | 2.46 | ECL deviates 0.001 | Reference 0.002 |
| 9.094 | 1674 | 0.041 | 0.937 | 15.773 | 16:1 w9c........ | 0.69 | ECL deviates -0.001 | |
| 9.162 | 3300 | 0.034 | 0.936 | 15.816 | 16:1 w7c........ | 1.35 | ECL deviates -0.001 | |
| 9.225 | 33564 | 0.038 | 0.935 | 15.857 | Sum In Feature 4. | 13.74 | ECL deviates 0.001 | 16:1 w7t/15i2OH |
| 9.452 | 69510 | 0.038 | 0.931 | 16.002 | 16:0 ............ | 28.34 | ECL deviates 0.002 | Reference 0.002 |
| 10.167 | 2622 | 0.041 | 0.920 | 16.434 | 16:0 10 methyl... | 1.06 | ECL deviates 0.001 | |
| 10.760 | 5106 | 0.050 | 0.912 | 16.792 | 17:1 w8c ........ | 2.04 | ECL deviates 0.000 | |
| 10.967 | 3912 | 0.041 | 0.910 | 16.917 | 17:1 w5c......... | 1.56 | ECL deviates -0.001 | |
| 11.106 | 3858 | 0.042 | 0.908 | 17.001 | 17:0 ............ | 1.53 | ECL deviates 0.001 | Reference 0.001 |
| 11.803 | 4014 | 0.041 | 0.900 | 17.411 | 17:0 10 methyl .. | 1.58 | ECL deviates 0.001 | |

| | | | | | |
|---|---|---|---|---|---|
| 12.410 | 34536 | 0.040 | 0.893 | 17.767 | 18:1 w9c ... 13.50 ECL deviates −0.002 |
| 12.499 | 600 | 0.038 | 0.892 | 17.820 | Sum In Feature 7 . 0.23 ECL deviates −0.002 18:1 w7c/w9t/w12t |
| 12.806 | 2670 | 0.051 | 0.889 | 18.000 | 18:0 ... 1.04 ECL deviates 0.000 Reference 0.001 |
| 13.474 | 45924 | 0.040 | 0.883 | 18.391 | TBSA 10Me18:0 .. 17.75 ECL deviates −0.001 |
| 13.769 | 792 | 0.054 | : | 18.564 | : |
| 14.095 | 1962 | 0.058 | 0.877 | 18.755 | Sum In Feature 8 . 0.75 ECL deviates −0.001 unknown 18.756/19:1 |
| 14.279 | 666 | 0.048 | 0.875 | 18.863 | Sum In Feature 9 . 0.26 ECL deviates −0.004 19:0 CYCLO w10c/un |
| 14.504 | 14016 | 0.041 | 0.874 | 18.995 | 19:0 ... 5.36 ECL deviates −0.005 Reference −0.004 |
| 15.533 | 900 | 0.049 | : | 19.601 | : |
| 16.215 | 5526 | 0.046 | 0.860 | 20.003 | 20:0 ... 2.08 ECL deviates 0.003 Reference 0.006 |
| 17.527 | 1722 | 0.051 | : | 20.776 | : > max rt |
| 17.628 | 2886 | 0.045 | : | 20.835 | : > max rt |
| 17.899 | 34308 | 0.046 | : | 20.995 | : > max rt |
| 18.444 | 174 | 0.015 | : | 21.316 | : > max rt |
| 18.509 | 288 | 0.029 | : | 21.354 | : > max rt |
| 18.681 | 2910 | 0.029 | : | 21.455 | : > max rt |
| 18.838 | 636 | 0.036 | : | 21.553 | : > max rt |
| 18.895 | 960 | 0.027 | : | 21.587 | : > max rt |
| 19.065 | 4800 | 0.026 | : | 21.687 | : > max rt |
| 19.466 | 1104 | 0.069 | : | 21.924 | : > max rt |
| 19.547 | 306 | 0.024 | : | 21.971 | : > max rt |
| 19.602 | 1878 | 0.034 | : | 22.004 | : > max rt |
| 19.676 | 2706 | 0.027 | : | 22.048 | : > max rt |
| 19.710 | 7452 | 0.028 | : | 22.068 | : > max rt |
| 19.767 | 5442 | 0.031 | : | 22.101 | : > max rt |
| 19.885 | 14460 | 0.028 | : | 22.171 | : > max rt |
| ****** | 33564 | | | | SUMMED FEATURE 4 . 13.74 15:0 ISO 20H/16:1w7t 16:1 w7t/15:20H |
| ****** | 600 | | | | SUMMED FEATURE 7 . 0.23 18:1 w7c/w9t/w12t 18:1 w9c/w12t/w7c |
| | | | | | 18:1 w12t/w9t/w7c |
| ****** | 1962 | | | | SUMMED FEATURE 8 . 0.75 unknown 18.756/19:1 19:1 w11c/unk 18.756 |
| ****** | 666 | | | | SUMMED FEATURE 9 . 0.26 un 18.846/18.858 un 18.858/.846/19cy |

FIG. 1B

| Solvent Ar | Total Area | Named Area | % Named | Total Amnt | | | 19:0 CYCLO w10c/un |
|---|---|---|---|---|---|---|---|
| 351695400 | 251748 | 250056 | 99.33 | 228421 | | | |

| | | Nbr Ref | ECL Deviation | Ref ECL Shift |
|---|---|---|---|---|
| | | 7 | 0.002 | 0.003 |

TSBA [Rev 3.80] Rhodococcus . . . . . . . . . . . . . . . . . . . . . . . . . . . . 0.115
    R. globerulus . . . . . . . . . . . . . . . . . . . . . . . . . . . 0.115
    R. g. GC subgroups B . . . . . . . . . . . . . . . . . . . 0.115
    R. equi . . . . . . . . . . . . . . . . . . . . . . . . . . . . . . . 0.070
    R. e. GC subgroup B . . . . . . . . . . . . . . . . . . . . 0.070
    R. erythropolis . . . . . . . . . . . . . . . . . . . . . . . . 0.065 (some 48h)
    Nocardia . . . . . . . . . . . . . . . . . . . . . . . . . . . . . 0.114
    N. globerula . . . . . . . . . . . . . . . . . . . . . . . . . . 0.114
    N. restricta . . . . . . . . . . . . . . . . . . . . . . . . . . . 0.084

CLIN [Rev 3.80] Rhodococcus . . . . . . . . . . . . . . . . . . . . . . . . . . . . 0.101
    R. rhodochrous . . . . . . . . . . . . . . . . . . . . . . . 0.101
    R. equi . . . . . . . . . . . . . . . . . . . . . . . . . . . . . . . 0.101
    R. erythropolis . . . . . . . . . . . . . . . . . . . . . . . . 0.101

RHIZ-1 [Rev 1.0] * NO MATCH *

FIG. 1C

| Data File Name | : C:\HPCHEM\1\DATA\RAW\020F1564.D | | |
|---|---|---|---|
| Operator | : Arlette | Page Number | : 1 |
| Instrument | : MIDI | Vial Number | : 20 |
| Sample Name | : cap inlet sample | Injection Number | : |
| Run Time Bar Code | : | Sequence Line | : |
| Acquired on | : 03 Oct 96  03:01 PM | Instrument Method | : $MIDI$A.MTH |
| Report Created on | : 03 Oct 96  03:25 PM | Analysis Method | : $MIDI$A.MTH |
| Sample Info | : DATA:C96A02775A (2906) | | |

RHODOCOCCUS GLOBERULUS STRAIN FOR CONTROLLING CORN ROOTWORM

FIELD OF THE INVENTION

This invention is in the field of biopesticides. More particularly, the present invention describes a novel, pesticidal strain of *Rhodococcus globerulus* that is active against corn rootworm, e.g., *Diabrotica virgifera, D. longicornis, D. undecimpunctata*. The novel *Rhodococcus globerulus* strain also produces a metabolite in the supernatant of a whole broth culture that is useful as a biocontrol agent in the treatment and prevention of corn rootworm infestation of plants.

BACKGROUND OF THE INVENTION

Every year 250–300 million dollars of chemical pesticides are used to control corn rootworm infestations. Many of these chemical pesticides are toxic to humans, wildlife and other nontarget species. In addition, some of these pesticides have been found in ground water. New chemical pesticides cost $100 million to develop.

Biological control offers an attractive alternative to synthetic chemical pesticides. Biopesticides (living organisms and the naturally-occurring compounds produced by these organisms) can be safer, more biodegradable, and less expensive to develop.

One commonly used biopesticide is the gram-positive bacterium *Bacillus thuringiensis*. Pesticidal *B. thuringiensis* strains are known to produce crystal proteins during sporulation that are specifically toxic to certain orders and species of insects and nematodes (See, e.g., U.S. Pat. Nos. 4,999,192 and 5,208,017). Proteinaceous endotoxins produced by *B. thuringiensis* also act as insecticidal agents against corn rootworm and other beetles (e.g., U.S. Pat. No. 5,187,091, and Johnson et al. (1993) *J. Economic Entomology*, 86: 330–333). *B. thuringiensis* endotoxins have been shown to be effective pesticides in the form of purified crystals, washed cell pellets, and expressed proteins. Warren et al. (WO 96/10083) discloses non-endotoxin proteins produced during the vegetative stage of *Bacillus cereus* and *B. thuringiensis*. These vegetative proteins, designated Vip1 and Vip2, have potent insecticidal activity against corn rootworm (northern and western) (Estruch et al. (1997) *Nature Biotechnology* 15:137–141 and Mullins et al. (1997) *Appl Environ. Microbiol.* 63 (in press).

One *B. thuringiensis* thermostable-metabolite designated beta-exotoxin has also been shown to have pesticidal properties. Burgjeron and Biache (1979) *Entomophaga II*:279–284 report a beta exotoxin that is active against Colorado potato beetle (*Leptinotarsa decemlineata*). In addition, the known *B. thuringiensis* beta-exotoxins exhibit non-specific pesticidal activity, killing not only nematodes, but also flies, armyworms, mites, and corn rootworms. Sigma-exotoxin has a structure similar to beta-exotoxin, and exhibits pesticidal activity against Colorado potato beetle (Argauer et al. (1991) *J. Entomol. Sci.* 26:205–213). Alpha-exotoxin is toxic to larvae of *Musca domestics* (Luthy (1980) *FEMS Microbiol. Lett.* 8:1–7). Gamma-exotoxins are various proteolytic enzymes, chitinases and proteases. The toxic effects of gamma-exotoxins are only expressed in combination with beta-exotoxin or delta-endotoxin. Forsberg et al. (1976) "*Bacillus thuringiensis*: Its effects in Environmental Quality," National Research Council of Canada. Stonard et al. (1994) *ACS Symposium Series* 551: 25 report a water-soluble secondary metabolite exhibiting pesticidal activity against corn rootworm in the supernatant of a *Bacillus cereus* strain.

There are no documented strains of Rhodococcus sp. that produce metabolites exhibiting pesticidal activity against corn rootworms. Moreover, there are no known solvent-extractable metabolites produced by Rhodococcus sp. with pesticidal activity against corn rootworms.

BRIEF DESCRIPTION OF THE DRAWINGS

FIGS. 1 and 2 show MIDI profiles of AQ719.

DISCLOSURE OF THE INVENTION

Figure 2:
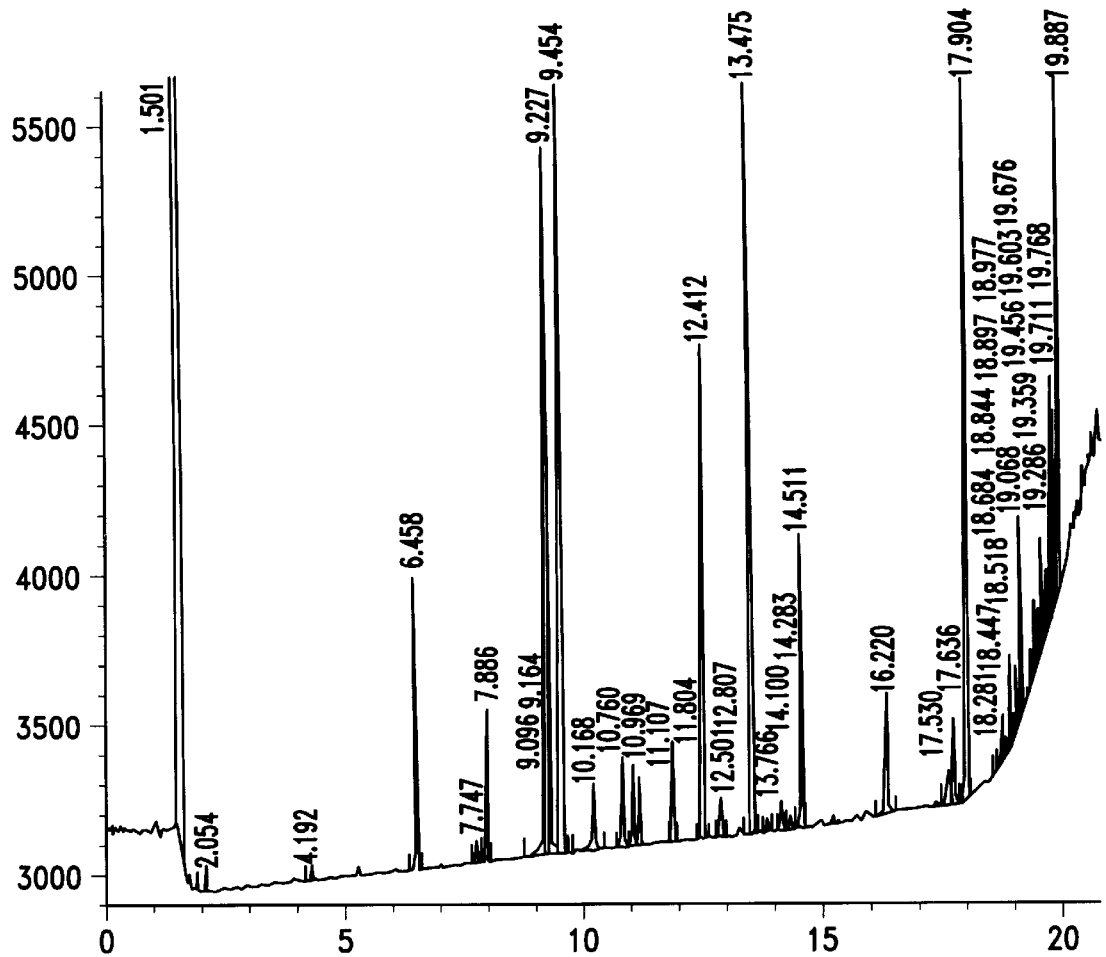

A novel strain of *Rhodococcus globerulus* strain AQ 719 is provided that produces a metabolite that exhibits pesticidal activity against corn rootworms. Also provided is a method for treating or protecting a plant from corn rootworm infestations comprising applying an effective amount of the novel metabolite-producing bacterial strain, a supernatant containing such a metabolite obtained from a whole broth culture of the strain or the metabolite itself to the plant or its environment.

MODES OF CARRYING OUT THE INVENTION

The present invention provides a novel strain of *Rhodococcus globerulus* and mutants and variants thereof that produces a metabolite that exhibits pesticidal activity against corn rootworms, nematodes and beet armyworms. The novel strain is designated *Rhodococcus globerulus* AQ719 and was deposited with the NRRL on Mar. 7, 1997 under the provisions of the Budapest Treaty on the International Recognition of the Deposit of Microorganisms for the Purpose of Patent Procedure under Accession Nos. B-21663. The invention also includes a solvent-extractable metabolite with pesticidal activity against corn rootworms that is produced by the novel strain. The invention further includes methods of protecting or treating a plant from corn rootworm infestation comprising applying a bacterial suspension of strain AQ719 or a metabolite-containing supernatant of a culture of strain AQ719 or purified a metabolite produced by the novel strain AQ719 to the plant or its environment.

DEFINITIONS

As used herein, "biological control" is defined as control of a pathogen or insect by the use of a second organism.

The term "bacteria" includes any prokaryotic organism that does not have a distinct nucleus.

The term "culturing" refers to the propagation of organisms on or in media of various kinds.

"Whole broth culture" refers to a liquid culture containing both cells and media.

"Supernatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the insect infestation.

As used herein, the term "insects" includes all organisms in the class "Insecta."

"Pre-adult" insects refers to any form of an organism prior to the adult stage, including, for example, eggs, larvae, and nymphs.

"Insecticidal" refers to the ability of a substance to increase mortality or inhibit growth rate of insects.

"Nematicidal" refers to the ability of a substance to increase mortality or inhibit the growth rate of nematodes.

"Pesticidal" refers to the ability of a substance to increase mortality or inhibit the growth rate of insects, nematodes and mites.

"Positive control" means a compound known to have pesticidal activity. "Positive controls" include, but are not limited to commercially available chemical pesticides.

The term "negative control" means a compound known not to have pesticidal activity. Examples of negative controls are water or ethyl acetate.

The term "solvent" includes any liquid that holds another substance in solution. "Solvent extractable" refers to any compound that dissolves in a solvent and which then may be isolated from the solvent. Examples of solvents include, but are not limited to, organic solvents like ethyl acetate.

The term "metabolite" refers to any compound, substance or byproduct of a fermentation of a microorganism that has pesticidal activity.

We describe a novel metabolite-producing bacterial strain of *Rhodococcus globerulus* that kills or stunts corn rootworm larvae.

In one aspect, the present invention provides a method for treating or protecting a plant from corn rootworm infestations comprising applying an effective amount of a supernatant obtained from a whole broth culture of *Rhodococcus globerulus* AQ719 to the plant which includes all portions of the plant and its roots or to its environment which includes the soil surrounding the plant. The supernatant may be obtained by methods well known in the art including centrifugation, filtration, sedimentation and the like.

In another aspect, the invention encompasses a method of treating or protecting a plant from corn rootworm infestations comprising applying an effective amount of the whole broth culture of the novel strain of *Rhodococcus globerulus* to a plant which includes any portion of the plant and its roots or to its environment which includes the soil surrounding the plant.

In yet another aspect of the invention, a method is provided for treating or protecting a plant from corn rootworm infestations comprising applying an effective amount of a supernatant containing a metabolite produced by the novel strain of *Rhodococcus globerulus* to a plant, which includes any portion of the plant and its roots or to its environment which includes the soil surrounding the plant.

In a further aspect of the invention, a method is provided for treating or protecting a plant from corn rootworm infestations comprising applying an effective amount of a metabolite produced by the novel strain of *Rhodococcus globerulus* to a plant which includes any portion of the plant or its roots or to its environment which includes the soil surrounding the plant.

In yet a further aspect of the invention, a method is provided for treating or protecting a plant from corn rootworm infestations comprising applying an effective amount of a composition comprising a metabolite produced by the novel strain of *Rhodococcus globerulus* to the plant which includes any portion of the plant and its roots or to its environment which includes the soil surrounding a plant.

In still another aspect of the invention, a method is provided for treating or protecting a plant from corn rootworm infestations comprising applying an effective amount of a composition comprising the novel strain of *Rhodococcus globerulus* to the plant which includes any portion of the plant or its roots or to its environment which includes the soil surrounding a plant.

In order to achieve good dispersion and adhesion of compositions, metabolites, whole broth cultures or supernatants within the present invention, it may be advantageous to formulate the composition, whole broth culture, supernatant and/or metabolite with components that aid dispersion and adhesion. Suitable formulations will be known to those skilled in the art.

Compositions, whole broth cultures, supernatants and/or metabolites within the present invention can be formulated as wettable powders, granules and the like, or can be microencapsulated in a suitable medium and the like. Examples of other formulations include, but are not limited to soluble powders, wettable granules, dry flowables, aqueous flowables, wettable dispersible granules, emulsifiable concentrates and aqueous suspensions. Other suitable formulations will be known to those skilled in the art.

All patents and publications cited herein are incorporated by reference The following examples are provided to illustrate the invention. These examples are not to be construed as limiting.

EXAMPLES

Example 1

Characterization of Strain AQ719

Isolates were identified based on whole-cell cellular fatty acids, derivatized to fatty acid methyl esters (FAMEs) (Miller, L. T. (1982) "Single derivatization method for routine analysis of bacterial whole cell wall fatty acid methyl esters, including hydroxy acids," *J. Clin. Microbiol.* 16:584–586) and analyzed by gas chromatography using the MIDI system (Microbial Identification System, Inc., Newark, Del.). The procedure and protocols used for growing the bacterial cultures and instrument specification are described by MIDI ("Identification of bacteria by gas chromatography of cellular fatty acids," Technical Note #101, MIDI Inc., Newark, Del.) Isolates were grown on tryptic soy agar plates (TSA) (BBL) at 28° C. for 24 hours and the cells were harvested. One mL of a methanolic NaOH (15% [wt/vol] NaOH in 50% [vol/vol] methanol) was added and cells were saponified at 100° C. for 30 minutes. Esterification of fatty acids was performed with 2 mLs of 3.25 N HCl in 46% (vol/vol) methanol at 80° C. for 10 minutes. The FAMEs were extracted into 1.25 mL of 1:1 (vol/vol) methyl-tertbutyl ether-hexane, and the organic extract washed with 3 mL of 1.2% (wt/vol) NaOH before analysis by gas chromatography. The GC (Hewlett-Packard 5890A) was equipped with a flame ionization detector and capillary column (Hewlett-Packard no. 19091B-102 (Cross-linked 5% phenyl-methyl silicone; 25 m×0.22 mm ID; film thickness, 0.33 µm; phase ratio, 150) with hydrogen as the carrier gas. FAME peaks were automatically integrated by a Hewlett-Packard 3392 integrator and bacterial isolates named using the MIDI Microbial Identification Software (Sherlock TSBA Library version 3.80). The FAME profile of *Xanthomonas maltophila* ATCC 13637 was used as reference check for the MIDI determinations.

The actual MIDI profiles of the strains are shown in FIGS. 1–2. AQ719 was identified as *Rhodococcus globerulus* with a similarity index of 0.115 and 0.116 in two separate tests.

Example 2

Activity of *Rhodococcus globerulus* AQ719 Against Corn Rootworm

Bacillus samples were grown in a Bacillus culture medium designated medium 3. Medium 3 contained 3 g dextrose, 20 g peptone, 3 g yeast extract, 1.5 g Proflo™ (cottonseed flour), 5 mLs of a solution (3.66 g $CaCl_2.2H_2O$ per 100 mLs), 5 mLs of a salt solution (2.46 g $MgSO_4.7H_2O$, 0.046 g $MnCl_2$, 0.28 g $ZnSO_4.7H_2O$, 0.4 g $FeSO_4.7H_2O$ per 100 mLs), 3.4 g $KH_2PO_4$ and 4.35 g $K_2HPO_4$. One day old streaked cultures were used to inoculate 250 mL baffled shake flasks. Flasks were shaken at 210 rpm at 29° C. for 3 days. To assay insecticidal activity, 5 mLs of culture broth were centrifuged at 5,200 rpm for 20 minutes and the supernatant used in the microassay described below.

Assays were performed in 96-well microplates. Each well contained a solid agar substrate, a test organism and either a positive control, a negative control or supernatant obtained as described in Example 1 from the novel strains.

To assay insecticidal activity, an agar substrate was prepared for the wells of the microplate according to Marrone et al. (1985) *J. Econ. Entomol.* 78: 290–293. To assay nematicidal activity, plain agar (1.5%) was used in the wells instead.

A 1 ppm solution of Avid® (avermectin) was used as a positive control. Deionized water was used as a negative control. Two replicates of test sample or control were used for each assay. 40 µL of supernatant sample or whole broth grown in medium 1 or 3 were dispensed into each sample well. Plates were then placed in a fame hood to dry for approximately 2–3 hours until the agar solution was dried.

Test organisms were either pre-adult corn rootworms (*Diabrotica undecimpunctata*), pre-adult German cockroaches (*Blatella germanica*), pre-adult beet armyworms (*Spodoptera exigua*), pre-adult flies (*Drosophila melanogaster*), or the N2 strain of the nematode *Caenorhabditis elegans*. Test organisms were diluted in 0.1% agar to a concentration of approximately 5 organisms per 25 µL of agar dispensed into each well. The microplate was sealed with an airtight substance such as Mylar®, and each well ventilated with a pin press. The plates were incubated at 27° C. for up to 7 days.

After incubation, wells were scored by noting neonate mortality or the degree of larval development. Sample wells containing all dead or stunted larvae were given a score of 1, wells containing some dead and other severely stunted larvae were given a score of 2, live but stunted larvae were scored as 3 and sample wells containing no dead larvae were given a score of 4. Scores were averaged among replicates within each sample. Results are summarized in Table 1.

TABLE 1

Score Rating of *Rhodoeoccus globerulus* AQ 719 Against Insect Pests Medium 3

|  | C. elegans | Corn rootworm | Beet armyworm | Fruit Fly | German Cockroach | Positive Control | Negative Control |
|---|---|---|---|---|---|---|---|
| Supernatant | 4.0 | 3.0 | 4.0 | NT | 4.0 | 1.0 | 4.0 |
| Whole Broth | NT | 2.0 | 4.0 | 4.0 | 4.0 | 1.0 | 4.0 |

NT = not tested

Example 3

Chemical Properties of the *Rhodococcus globerulus* AQ719 Metabolite Active Against Corn Rootworm To determine if the metabolite produced by the AQ719 strain was extractable in ethyl acetate, 50 mLs of medium 3 was inoculated with AQ719. 50 mLs of ethyl acetate was added to the culture of AQ719 and the mixture was shaken in a separatory funnel for 2 minutes. The aqueous layer was removed and the organic layer was collected in a bottle containing magnesium sulfate. The organic filtrate was then filtered into a round bottom flask and the solvent removed on the rotovap.

For the bioassay, the dried organic extract was redissolved in 2.5 mLs acetone. A 40 µL aliquot was removed and diluted to 800 µL with 70% acetone/water. This is a 10× concentration of the organic extract. Serial dilutions were carried out to obtain samples for testing against neonate corn rootworm with percent mortality recorded of neonate larvae (1 per well in a microplate as prepared above) after 7 days. The results are recorded in Table 2.

TABLE 2

Activity of Ethyl Acetate Extract of the Metabolite Produced by the *R. globerulus* AQ719 Strain Against Corn Rootworm

| Sample |  | Percent Mortality |
|---|---|---|
| AQ719: | Organic extract 5X | 90 |
|  | Organic extract 1X | 92 |
|  | Whole broth | 67 |
|  | 70% acetone/water | 71 |
|  | Water | 27 |

The results show that the metabolite produced by the *Rhodococcus globerulus* AQ719 strain that kills corn rootworms is extractable in ethyl acetate.

What is claimed is:

1. A biologically pure culture of a strain of Rhodococcus having all the identifying characteristics of *Rhodococcus globerulus* strain AQ719, NRRL Accession No. B21663 or mutants thereof, which have pesticidal activity against corn rootworm.

2. A composition comprising the *Rhodococcus globerulus* strain of claim 1 that exhibits pesticidal activity against corn rootworm and a carrier.

3. The composition of claim 2, further comprising at least one chemical or at least one additional biological pesticide.

4. The composition of claim 1, further comprising at least one chemical or at least one additional biological pesticide.

5. The composition of claim 2 wherein the biologically pure culture of *Rhodococcus globerulus* is formulated as a wettable powder or granule or a flowable on is microencapsulated.

6. The composition of claim 1 wherein the biologically pure culture of *Rhodococcus globerulus* is formulated as a wettable powder or granule or a flowable on is microencapsulated.

7. A biologically pure culture of *Rhodococcus globerulus* strain AQ719, NRRL Accession No. B21663.

8. A composition comprising the culture of claim 7 and a carrier.

9. The composition of claim 8, further comprising at least one chemical or at least one additional biological pesticide.

10. The composition of claim 7, further comprising at least one chemical or at least one additional biological pesticide.

* * * * *

UNITED STATES PATENT AND TRADEMARK OFFICE
CERTIFICATE OF CORRECTION

PATENT NO. : 6,027,723
DATED : Feb. 22, 2000
INVENTOR(S) : Heins et al

It is certified that error appears in the above-identified patent and that said Letters Patent is hereby corrected as shown below:

Page 1, column 1, under "Other Publications" the first reference (Johnson) should read --*J. Economic Entomology*--.

Column 4, line 23, the period was omitted at the end of the sentence.

Column 5, line 7, "$H_2O$" should read --$H_2O$--; line 8, "$H_2O$" should read --$H_2O$--; line 9, both occurrences, "$H_2O$" should read --$H_2O$--; and line 10, "$H_2O$" should read --$H_2O$--

Column 5, Table 1, "*Rhodoeoccus*" should read --*Rhodococcus*--.

Claim 1, line 1, "Rhodococcus" should be --*Rhodococcus*--.

Claim 5, line 3, "on" should be --or--.

Claim 6, line 3, "on" should be --or--.

Signed and Sealed this

Eighth Day of May, 2001

*Attest:*

NICHOLAS P. GODICI

*Attesting Officer*   Acting Director of the United States Patent and Trademark Office